(12) United States Patent
Howard et al.

(10) Patent No.: US 7,805,975 B2
(45) Date of Patent: Oct. 5, 2010

(54) GASLESS CALIBRATION IN METABOLIC GAS ANALYZERS

(75) Inventors: C. Peter Howard, Humboldt, TN (US); Yu Chen, Andover, MA (US); Michael G. Snow, White Bear Lake, MN (US)

(73) Assignee: Medical Graphics Corporation, St. Paul, MN (US)

( * ) Notice: Subject to any disclaimer, the term of this patent is extended or adjusted under 35 U.S.C. 154(b) by 515 days.

(21) Appl. No.: 11/899,335

(22) Filed: Sep. 5, 2007

(65) Prior Publication Data

US 2009/0056409 A1    Mar. 5, 2009

(51) Int. Cl.
G01N 33/00 (2006.01)
(52) U.S. Cl. .......................... 73/1.07; 73/1.02; 73/1.57; 73/1.59; 73/1.62; 73/1.88
(58) Field of Classification Search ................... 73/1.01, 73/1.02, 1.06, 1.07, 1.57, 1.59, 1.62, 1.88
See application file for complete search history.

(56) References Cited

U.S. PATENT DOCUMENTS

| | | | |
|---|---|---|---|
| 4,463,764 A | 8/1984 | Anderson et al. | |
| 5,042,500 A * | 8/1991 | Norlien et al. | 600/532 |
| 5,297,558 A | 3/1994 | Acorn et al. | |
| 5,510,269 A * | 4/1996 | Black et al. | 436/164 |
| 5,542,284 A * | 8/1996 | Layzell et al. | 73/23.2 |
| 5,583,339 A | 12/1996 | Black et al. | |
| 6,554,776 B1 | 4/2003 | Snow et al. | |

* cited by examiner

*Primary Examiner*—Daniel S Larkin
(74) *Attorney, Agent, or Firm*—Thomas J. Nikolai; Nikolai & Mersereau P.A.

(57) ABSTRACT

A method of calibrating a metabolic analyzer incorporating an oxygen analyzer and a NDIR carbon dioxide analyzer in the field that does not require the use of gas cylinders containing gases of known concentration is described. In calibrating the $CO_2$ detector, at the time of factory setup, the detector output for a gas of a known concentration is measured and stored in the memory of the metabolic analyzer's microprocessor, as is the detector output voltage when the IR source is dimmed by a known percentage. Subsequently, in the field, $CO_2$ levels in ambient air and cell pressure are measured at two different flow rates through the sample chamber and the IR source is again dimmed by the same percentage as had been used at the time of factory setup. Based upon the resulting readings, both the zeroing and span adjustment factors can be computed.

2 Claims, 4 Drawing Sheets

US 7,805,975 B2

GASLESS CALIBRATION IN METABOLIC GAS ANALYZERS

BACKGROUND OF THE INVENTION

I. Field of the Invention

This invention relates generally to measurement of respiratory gases using metabolic gas analyzers, and more particularly to a new method for calibrating such instruments in the field in a way that does not require the use of a reference gas and a calibration gas.

II. Discussion of the Prior Art

Traditional measurements of metabolic and respiratory variables during exercise require a spirometer to measure ventilation volume and gas analyzers to measure the fraction concentration of inspired and expired oxygen ($FIO_2$, $FEO_2$) and carbon dioxide ($FICO_2$, $FECO_2$). More recent developments of these metabolic gas analyzers has permitted the automated breath-by-breath measurement of oxygen uptake ($VO_2$) and carbon dioxide production ($VCO_2$) as well as gas exchange kinetics.

Subsequent development of faster analyzers and the incorporation of microprocessors have permitted the automation of breath-by-breath measurement of $VO_2$ and $VOC_2$, which provides real time reflection of gas exchange kinetics as well as steady state values. Metabolic analyzer systems, such as that described in U.S. Pat. No. 4,463,764 to Anderson et al., generally incorporate real-time analysis of oxygen, carbon dioxide and flow assessment for the primary inputs with microprocessor correction for changes in analyzer outputs, response time and environmental changes. These measurements are used to evaluate exercise performance, to prescribe personalized training protocols, to evaluate energy expenditure requirements at rest and with exercise, and to determine substrate utilization, i.e., fat burning vs. carbohydrate burning. U.S. Pat. No. 5,297,558 by Acorn et al. and U.S. Pat. No. 6,554,776 by Snow et al. describe two such systems.

During measurements, the flow and gas signals have independent response times, linearity and gains. The gas analyzer's response times must be aligned with the flow signal response, scaled for calibration and integrated to determine the change in volume of oxygen and carbon dioxide for each breath. In accordance with the prior art, calibration is generally performed using two gas mixtures of known concentration, one being 21.0% $O_2$, 0% $CO_2$ and the other being 12.0% $O_2$ with 5.0% $CO_2$.

The conventional $CO_2$ analyzer is commonly based on the principal of directing a source of infrared radiation along an optical path with a detector positioned on the opposite side. A sample chamber is positioned between the infrared source and the detector. The sample chamber will be made to contain the component gas to be analyzed. The $CO_2$ measurement is based on the absorption of infrared radiation at a specific wavelength due to the presence of $CO_2$ within the sample chamber. Gases, such as $O_2$ and $N_2$ which do not absorb at that wavelength will not change the absorption level. Higher levels of $CO_2$ absorb proportionally more of the infrared radiation which thereby decreases the output signal level from the infrared detector.

A known, prior art oxygen sensor commonly used in metabolic analyzers comprises a galvanic cell that consists of two electrodes in contact with a liquid or semi-solid basic electrolyte. The cell electrodes are made of dissimilar metals, such as silver and lead. When a gas sample is introduced into the cell, it diffuses through a membrane, usually made out of a Teflon polymer. The oxygen in the sample contacts the silver cathode and is chemically reduced to hydroxyl ions. The hydroxyl ions then flow toward the lead anode, where an oxidation reaction occurs with the lead. This oxidation/reduction reaction results in a flow of electrons proportional to the oxygen concentration of the sample. The electron flow (current) is measured by an external metering circuit connected to the cell electrodes. This current is proportional to the rate of consumption of the oxygen and is indicated on a meter as a percentage or parts-per-million of oxygen in the sample.

One drawback of such galvanic sensors is that as they age, they have a tendency to loose accuracy due to changes in the cell membrane temperature. As a result, analyzers that use battery-type galvanic cells must be recalibrated on a frequent basis, sometimes as often as once-per-test, depending on the criticality of the application.

The traditional calibration of gas analyzers requires two known-concentration gases, with one being used as a "reference" or "zero" gas and the other as a "calibration" or "span" gas. Such gases are conventionally contained in two relatively heavy and cumbersome tanks. The first tank provides the zero gas while the second provides a known magnitude change. A calibration factor is established using the ratio of the voltage level divided by the gas concentration difference, such as, for example, 2.1 volts at 21% $O_2$/1.2 volts at 12% $O_2$.

Accurate measurements require regular calibration of the gas analyzers and such calibration is performed in the field by introducing gases with known concentrations which span the range of interest. For example, the calibration gases may comprise 21.0% oxygen, 0.0% carbon dioxide, 79.0% nitrogen in a first tank and 16.0% oxygen, 5.0% carbon dioxide and 79.0% nitrogen in a second tank. The first mentioned gas is chosen because it represents what a typical inspired concentration may be. The second gas mixture represents an approximate expired gas mixture.

During calibration, the gas mixture containing 0% carbon dioxide is used to determine the baseline offset voltage with no absorption, while the gas mixture containing 5.0% $CO_2$ determines the gain or effect of $CO_2$ on the output level expressed as a percent per volt.

For an oxygen analyzer, the higher concentration represents the baseline while the lower determines the gain. Analyzer response times are determined by switching between the two gases by activating a solenoid valve. The response of each analyzer is measured and determinations are made for transport time, analyzer response time (2-90%), total time to 50% response and the magnitude of the maximal change. Flow sensors are typically calibrated by assessing output without flow and injecting/withdrawing a known volume of gas using a calibrated syringe. Additionally, the response time of the gas to the change in concentration, i.e., phase delay, is of critical importance. There are two components to phase delay, namely, transport time and analyzer response time. The transport time is a function of moving the gas sample through the length of the sample line and delivering the sample to the analyzer. Once the sample reaches the analyzer, the inherent response time of the analyzer must be known.

It is the principal object of the present invention to provide a method for calibrating a metabolic gas analyzer in the field that does not require reference and calibration gas mixtures to zero, span, measure the analyzer response time and to automate the regular calibration process.

Another object of the present invention is to provide a method for calibrating a metabolic gas analyzer in field that obviates the need for having available heavy, cumbersome tanks for containing calibration gases in order to field calibrate the $CO_2$ and the $O_2$ sensor devices used in a metabolic analyzer.

SUMMARY OF THE INVENTION

The present invention provides a method for calibrating a metabolic analyzer of the type having a sample line adapted to receive inspiratory and expiratory respiratory gases therein, where the sample line is connected to a non-dispersive, infrared, $CO_2$ sensor. The $CO_2$ sensor has an infrared emitter and an infrared detector spaced from one another in the sample line. The sample line also leads to an $O_2$ sensor, preferably a galvanic cell-type oxygen sensor, that is located downstream of the $CO_2$ sensor. The method of the present invention further requires that there be a pump for drawing respiratory gases through the $CO_2$ sensor and the $O_2$ sensor. The metabolic analyzer further includes a pressure sensor for sensing the absolute pressure in the sample line. A flow regulator is provided for controlling the rate that the respiratory gases are being drawn by the pump through the sample line.

In carrying out the gasless calibration method, at the time of factory setup of a new metabolic analyzer, ambient air of a low carbon dioxide concentration is introduced into the sample line and the carbon dioxide detector output voltage signal corresponding to the known concentration is recorded. Next, a measurement of the ambient air with a higher level of $CO_2$ is taken and the detected output voltage measurement is also recorded. An ambient default gain factor is computed and corrected to sea level pressure by multiplying the gain factor by $760/P_{bar}$.

The pressure in the sample line is also measured before and after the flow regulator changes the rate of flow of the gas through the sample line from a first value to a second value. This may be accomplished by inserting two different orifice plates in the flow path or by changing the pump speed. The difference between the $CO_2$ concentrations as measured by the $CO_2$ sensor at the first rate of flow and at the second rate of flow are computed and recorded for later use at the time of field calibrations. Next, while still performing factory set-up, gas of a known $CO_2$ concentration is run through the sample tube and the IR detector output voltage for this concentration is measured. Next, the IR source is dimmed by a fixed percentage and the detector output is measured. The ratio of detector output due to dimming to detector output with the known gas is formed and corrected to standard sea level pressure.

Subsequently, when the metabolic analyzer is to be calibrated by a user in the field to zero, the user measures the ambient $CO_2$ concentration at two different pressures which are corrected to a standard pressure by multiplying the measured ambient concentration by a factor of 760/measured barometric pressure. The detector output ratio is then compared to the corresponding ratio value measured at the time of factory set-up that had been stored in the analyzer's memory. Any difference corresponds to the offset needed to zero.

To adjust the span, the infrared source within the $CO_2$ sensor—typically, an incandescent bulb—is dimmed by an amount corresponding to a change in $CO_2$ sensor output measured at the time of factory setup when the gas of known carbon dioxide concentration had been introduced into the sample line. Thus, the dimming acts as if the $CO_2$ gas of the known concentration had been introduced.

The field calibration steps further involve measuring the pressure in the sample line and the $CO_2$ detector output signal at two discrete rates of flow such as, for example, $F_1=60$ cc/min and $F_2-2F_1=120$ cc min, and determining the difference between the detector outputs at these two discrete flow rates. The difference value between the $CO_2$ concentration measured at the two discrete rates of flow recorded at the time of factory setup are then retrieved from the memory of a microprocessors controller allowing a determination of the actual ambient $CO_2$ level being measured in the field by solving the equation:

$$\text{Actual } CO_2 = CO_2 \text{ reading} \times \left(\frac{(V_{F2} - V_{F1})\text{Field}}{(V_{F2} - V_{F1})\text{Factory}}\right)\frac{760}{Pamb.}$$

where $V_{F2}$ is the voltage from IR detector at a flow of $F_2$ and $V_{F1}$ is the voltage at flow $F_1$.

A similar technique is employed in calibrating a galvanic cell-type oxygen analyzer. With this type of analyzer, it is known that a gas of zero $O_2$ concentration produces a zero output voltage signal from the cell and that a 100 percent oxygen gas will produce a known signal. A two-point calibration curve is thus defined. Arrival at the $O_2$ concentration in an ambient gas sample only involves accounting for relative humidity, barometric pressure and temperature at the field location so that the effect of water vapor in the ambient room air can be adjusted for. Knowing the relative humidity and barometric pressure and temperature, percent water vapor in air can be arrived at using physiometric tables stored in a processor's memory. The water vapor concentration in ambient air is prorated against the $O_2$ and $N_2$ and the actual $O_2$ concentration is calculated in arriving at the span.

Another factor of importance in using and interpreting the results obtained from a metabolic analyzer is whether there has been a significant change in phase delay between the time of initial factory testing thereof and its use in the field. In order to detect a change in phase delay, as a part of the calibration procedure, a step change is made in the sample flow rate and a corresponding measurement of the change in pressure relative to the change in flow rate is made. In that phase delay is linearly related to sample flow rate and the resistance in the sample line, knowing the pressure, one can calculate the phase delay by knowing the change in the ambient pressure within the sample tube occasioned by the change in flow rate that has been introduced. The thus-measured resistance can then be compared to the resistance of the sample line at the time of factory setup to determine whether the unit in the field requires cleaning or the like.

DESCRIPTION OF THE DRAWINGS

The foregoing features, objects and advantages of the invention will become apparent to those skilled in the art from the following detailed description of the preferred embodiment, especially when considered in conjunction with the accompanying drawing.

DESCRIPTION OF THE PREFERRED EMBODIMENT

Figure 1:
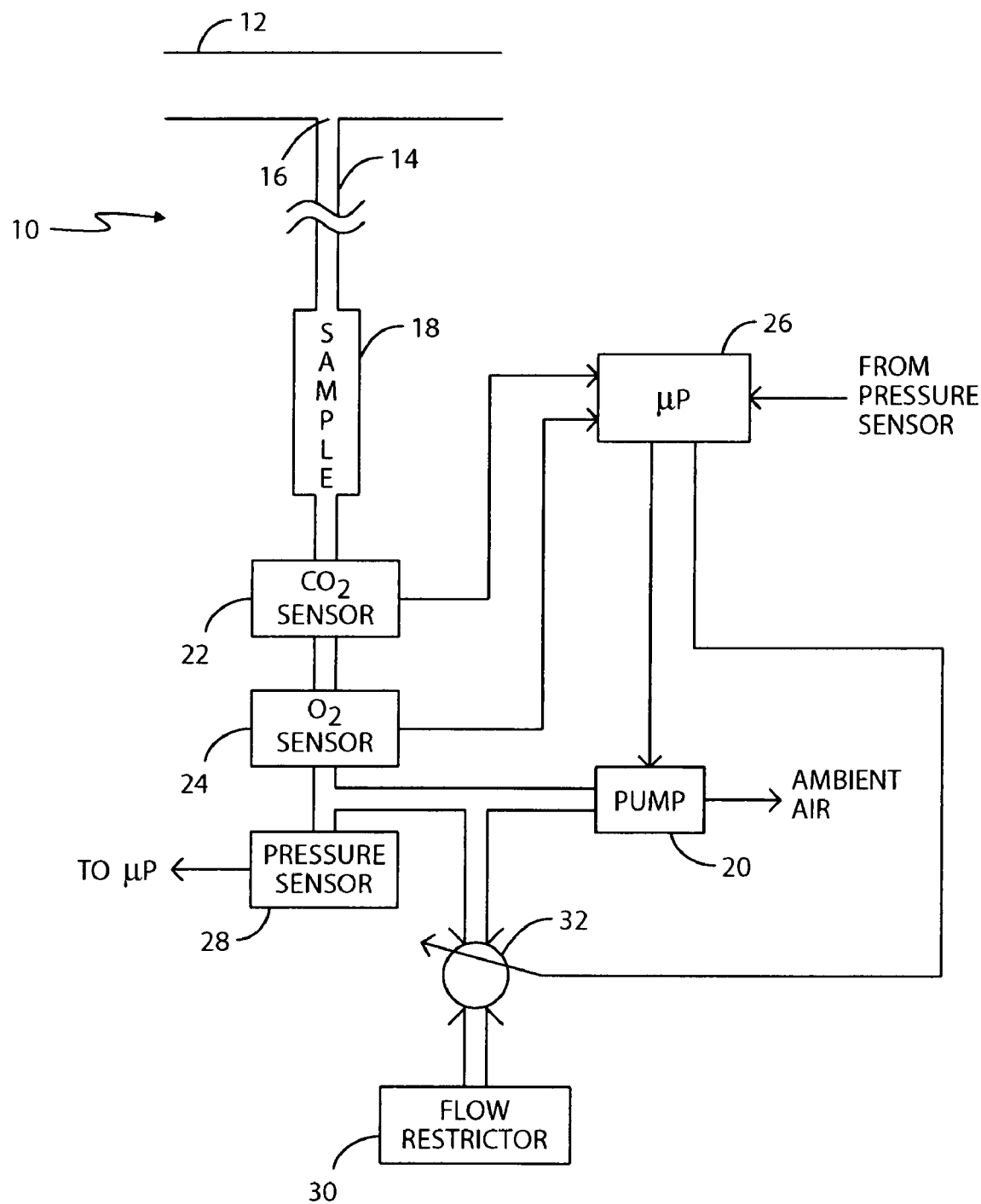
FIG. 1 is a schematic block diagram showing the components of a metabolic analyzer on which the gasless-calibration method of the present invention can be practiced.

Referring to FIG. 1, there is shown a schematic block diagram of a metabolic analyzer on which the calibration method of the present invention can be applied. The analyzer 10 includes a mouthpiece member 12 through which a subject is made to breath. A sample line 14 connects to a port 16 on the mouthpiece member and leads to a sample tube 18. The sample tube 18 is preferably a tube of a Nafion ionomer. The Nafion ionomer is highly permeable to water vapor. The sulfonic acid groups in Nafion have a very high water-of-hydration, allowing them to efficiently absorb water. Inner-connections between the sulfonic acid groups lead to very rapid transfer of water through the Nafion allowing it to selectively dry or to humidify gases. In the present application, water vapor in expired air permeates outwardly through the walls of the tube, thus effectively drying the respiratory gas flowing through it so as to match the ambient humidity.

A pump 20 is used to draw the respiratory gas through the sample line and through a series connection of a carbon dioxide sensor 22 and an oxygen sensor 24. The carbon dioxide sensor 22 is preferably a single-beam, non-dispersive, infrared-type (NDIA) sensor widely used for most metabolic measurements. The oxygen sensor 24 may be an electrochemical analyzer (fuel cell), a paramagnetic analyzer or a zirconia analyzer, all of which have found use in measurement of oxygen concentration in a gas sample.

A microprocessor 26 is connected to receive output signals from the carbon dioxide sensor 22 and the oxygen sensor 24 as well as a signal from an absolute pressure sensor 28. The pressure sensor 28 is provided and arranged to measure absolute barometric pressure when the pump 20 is off and to measure the pressure within the sample line when the pump is operational. The microprocessor 26 is used to calculate the oxygen and carbon dioxide concentration to control the gasless calibration method and to measure phase delay and sample flow rate when the pump 20 is on.

The metabolic analyzer 10 may also include a flow restrictor 30 comprising first and second critical orifices and a selector device 32. This arrangement will only permit flows of two discrete values, such as, for example, 60 cc/min and 120 cc/min, depending on which of the two orifices is placed in circuit with the pump 20. The selector device 32 is also switched by an output control from the microprocessor 26. Alternatively, a step-change in flow can be achieved by a step-change in pump speed.

A NDIR $CO_2$ sensor comprises an infrared source and an infrared detector spaced apart from one another in the sample tube through which a sample of respiratory gases may be drawn. The NDIR analyzer relies on the fact that carbon dioxide absorbs infrared radiation in a non-linear way in accordance with the Beer-Lambert Law such that as the concentration of $CO_2$ gas in a sample increases, the detector output signal decreases.

The oxygen sensor 24 is preferably an electrochemical fuel cell. It is absolute and linear so that a zero $O_2$ percentage concentration in a gas sample equals a zero output from the sensor. Based on relative measured humidity, temperature and $CO_2$ level, the oxygen concentration in room air can be calculated and the oxygen analyzer output is recorded. From the two points of known oxygen concentration and analyzer output (zero percent, room air), a linear model of oxygen concentration and analyzer output can be established. In that $O_2$ consumption by the body is the difference between inspired and expired oxygen, a small error in the actual ambient level will be reflected as a small error in the fraction of expired oxygen ($FeO_2$) in the same direction, but modified by the slope of the curve. In reality, the actual error is usually less than 0.1 percent. In that the oxygen sensor is a partial pressure device, ambient pressure changes are calibrated out with gasless calibration.

Figure 2A:
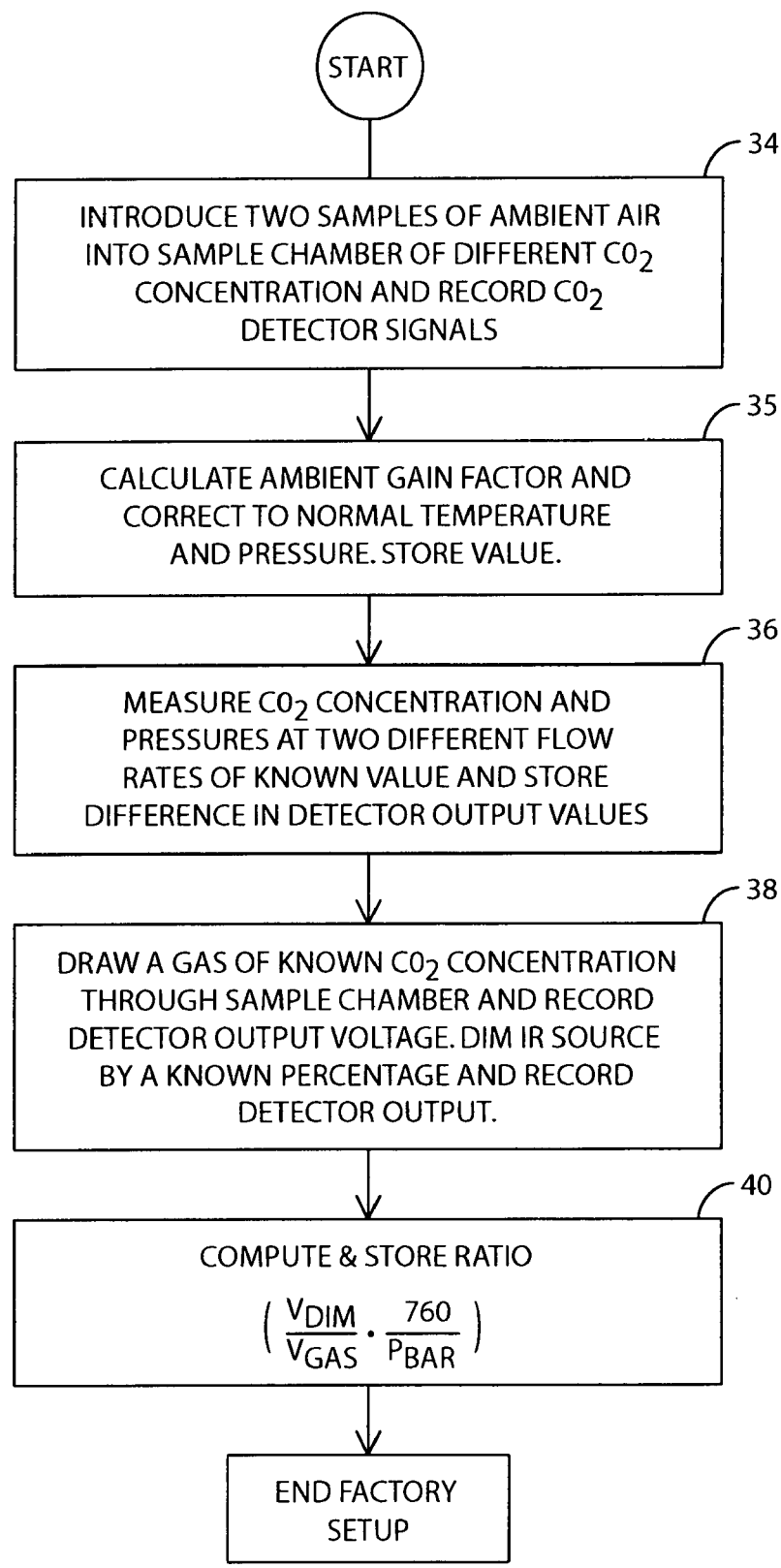
FIGS. 2(a) and 2(b) comprise a process flow chart outlining the steps for performing gasless calibration of a NDIR $CO_2$ sensor of metabolic analyzer.
Figure 2B:
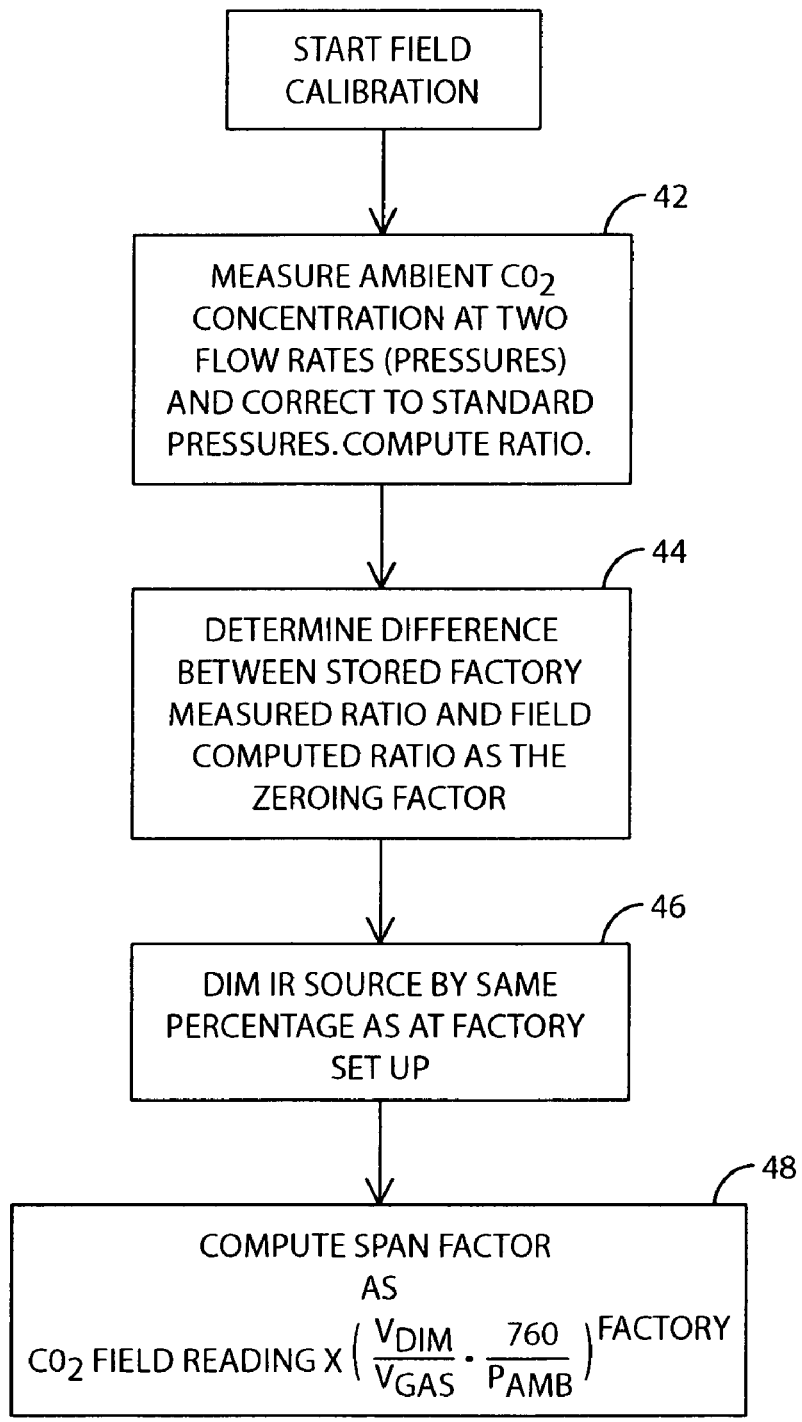

As stated in the discussion of the prior art, the objective of the present invention is to provide a method of calibration of a metabolic analyzer that obviates the need for gas cylinders containing known concentrations of $O_2$ and $CO_2$ and instead rely upon ambient air in the calibration process. FIG. 2(a) is a process flow chart showing the steps performed at the time of factory setup in carrying out gasless calibration of a NDIR $CO_2$ sensor. FIG. 2(b) shows the steps carried out at the time of field calibration of the $CO_2$ sensor. Block 34 shows that at the time that a new metabolic analyzer is constructed, a factory setup procedure is performed in which two samples of ambient air are made to enter the sample chamber and the $CO_2$ detector is used to measure the $CO_2$ concentration of each with the output voltage values being stored. An ambient gain factor is calculated and corrected to normal temperature and pressure with the result being stored (block 35). Next, pressure within the NDIR $CO_2$ analyzer is measured at two discrete gas sample flows, say, at $F_1$ cc/min and at $F_2=2 F_1$ cc/min (block 36). The corresponding pressure values may be referred to as $P_1$ and $P_2$. A known ambient $CO_2$ analyzer is used to measure the ambient $CO_2$ concentration level and this value is recorded, as is the pressure within the $CO_2$ cell at a gas sample flow of $F_1$ cc/min, via the selection of the appropriate critical orifice in the flow restrictor. The gas sample flow is then changed to $F_2=2 F_1$ cc/min, effectively doubling the pressure. The observed detector output voltage flow $F_1$ cc/min is recorded and the ratio $P_1/P_2$ is established. In that:

$$\frac{V_{F1}}{P_1} = \frac{V_{F2}}{P_2}$$

where $V_{F1}$ is the IR detector output at flow $F_1$ and $V_{F2}$ is the IR detector output at flow $F_2$.

Therefore:

$$V_{F1} = P_1 \times \frac{V_{F2}}{P_2}$$

In the factory, prior to the shipment of a metabolic analyzer 10 to the field, an optimized gain factor is determined by first recording the $CO_2$ detector output voltage when gas of a known $CO_2$ concentration is in the sample chamber and then dimming the infrared source by a known percentage and again noting the detector output. These measurements are recorded and stored in a memory of the microprocessor 26. See blocks 38 and 40 in FIG. 2(a).

When it is desired to calibrate the $CO_2$ sensor in the field, ambient air is drawn through the sample line and $CO_2$ levels and cell pressure are measured at the same time flow values used at the time of factory set-up, i.e., in our example, $F_1$ cc/min and again at 2 $F_1$ cc/min and the difference there between is measured. See blocks 42 and 44 in FIG. 2(b). That is:

$$V_{2F1} - V_{F1}$$

The measured observed values are corrected to standard pressure by multiplying same by the factor $760/P_{Bar}$ where $P_{Bar}$ is the barometric pressure at the calibration site.

Next, the infrared source is again dimmed by a predetermined, fixed percent as was used at the time of factory setup and the change $V_{2F1} - V_{F1}$ is computed (block 46). The corresponding reading obtained at the factory is read from the microprocessor memory and used to calculate the actual $CO_2$ concentration as show by block 48:

$$\text{Actual } CO_2 = CO_2 \text{ field reading} \left(\frac{V_{DIM}}{V_{GAS}}\right)^{factory} \times \frac{760}{Pamb}$$

where $V_{DIM}$ in the sensor output Voltage due to source dimming and $V_{GAS}$ is the sensor output voltage due to $CO_2$ concentration in the sample chamber.

A metabolic analyzer must also be able to determine a subject's oxygen uptake and, as such, will incorporate an oxygen sensor as a component part. As described above, a galvanic cell oxygen analyzer is well suited for use in a metabolic analyzer for measuring the absolute $O_2$ concentration in an ambient air sample.

It is known that absolute oxygen concentration varies with changes in barometric pressure and temperature. As barometric pressure decreases, or as temperature increases, air expands and the number of $O_2$ molecules per unit volume decreases. The opposite occurs as barometric pressure increases or as temperature decreases.

As the humidity in air increases, water vapor molecules displace $O_2$ molecules, causing the output of the sensor to decrease. The effect of humidity is larger at warmer temperatures because there is more water vapor in the air.

In calibrating the $O_2$ sensor, it is known that the galvanic cell produces a zero voltage output when the oxygen concentration is zero percent. A pure oxygen sample will produce a fixed voltage output reading. Therefore, the zero calibration is readily arrived at.

Figure 3:
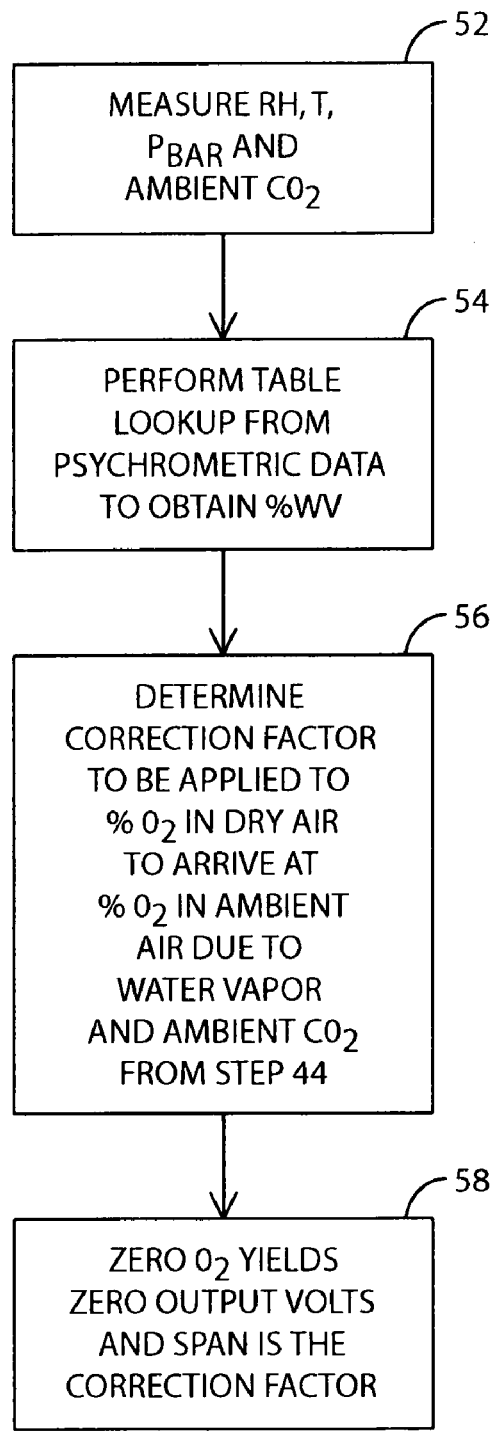
FIG. 3 is a flow chart for performing gasless calibration of a galvanic cell type $O_2$ analyzer in the field.

The span calibration involves the steps set out in the flow diagram of FIG. 3. The method presupposes that at the time of factory set-up, the memory of the microprocessor 26 is made to store a psychometric table whereby the percent of water vapor in an ambient air sample can be read from the table using barometric pressure, relative humidity and temperature as the input variables. Thus, as indicated by block 52 in FIG. 3, at the time of field calibration of the $O_2$ sensor, the relative humidity and temperature are measured. The pressure sensor 28 can be used to measure the barometric pressure at the time of calibration.

As represented by blocks 54 56 and 58, the obtained measured values of relative humidity, temperature and barometric pressure are used to read from the look-up table the applicable percentage of water vapor in the ambient air sample. It is a known constant that the concentration of oxygen in dry air is 20.93% and exhibits a partial pressure of 159 mm Hg at normal barometric pressure (760 mm Hg). To arrive at the actual $O_2$ concentration in ambient air, it is necessary to prorate the percentage water vapor against the percentage oxygen and percentage nitrogen in the air. See block 56.

As an example, if the temperature, barometric pressure and relative humidity cause a readout of percent water vapor equal to, say, 1.35% from the look-up table, and the ambient $CO_2$ concentration is equal to 0.1%, then the correction factor to be applied to the dry air quantity (20.93% $O_2$) may be computed by multiplying the water vapor percentage by 0.2093, the $CO_2$ percentage by 0.2093 and the nitrogen percentage by 0.2093, which yields a correction factor equal to the sum of these values, i.e., in the example given 0.465. This correction factor is subtracted from the concentration of oxygen in dry air to yield the actual $O_2$ concentration, i.e., 20.465%.

To determine whether there has been a change in flow resistance through the analyzer due to contamination or the like, at the time of factory set-up, the ratio of the pressures measured at two discrete flow rates, $P_1$ and $P_2$, are used to form a ratio. Later, at the time of field calibration, the same change in flow rates are made as were used during factory set-up and the corresponding pressures are again measured. If it turns out that the pressure ratios at factory set-up differ from the pressure ratios measured in the field, the phase delay can be adjusted accordingly since the difference is proportional to time lag.

As has been explained above, the method of the present invention permits calibration of the components of a metabolic analyzer in the field without the necessity of resorting to the use of reference and calibration gas supply cylinders.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A method of calibrating a metabolic analyzer having a sample line adapted to receive inspiratory and expiratory respiratory gas therein, the sample line connected to a non-dispersive infrared carbon dioxide sensor having an IR emitter and an IR detector spaced from one another in the sample line, an oxygen sensor in series with said carbon dioxide sensor, means for drawing the respiratory gases through the carbon dioxide sensor and the oxygen sensor, a pressure sensor for sensing absolute pressure in the sample line and a flow regulator controlling the rate that the respiratory gases are drawn and a microprocessor based controller operatively coupled in controlling relation to the IR emitter, the IR detector, the oxygen sensor, the pressure sensor and the flow regulator comprising the steps of:

(a) at the time of factory set-up:
  (i) introducing two samples of ambient air of differing $CO_2$ concentration into said sample line and storing resulting $CO_2$ detector output signals in a memory of the microprocessor based controller;
  (ii) calculating an ambient $CO_2$ gain factor corrected to normal temperature and pressure and store resultant value;
  (iii) measuring the $CO_2$ concentration and pressures in the sample line at two discrete flow rates of predetermined values and storing the difference in $CO_2$ detector output signal values and pressure sensor output signal valves;
  (iv) reducing current to IR emitter by a fixed percentage and record resulting $CO_2$ detector output signal;
  (v) computing and storing ratio of detector output signal due to dimming to detector output signal due to introduction of a known span gas introduction in step (a)(i) corrected to normal temperature and pressure;

(b) in the field:
  (i) measuring $CO_2$ concentration in ambient air sample drawn into sample line at a first flow rate and at a second flow rate;
  (ii) determining the difference between the ratio established in step (a)(iii) and step (b)(i) as the zero calibration factor;
  (iii) reducing the current to the IR emitter by the same fixed percentage as used in the step (a)(iv);
  (iv) comparing the ratio of outputs as established in step (a)(v) to those achieved in step (b)(iii); and
  (v) computing a span calibration factor as:

$$CO_2 \text{ reading from step } (b)(ii) \times \left(\frac{(V_{DIM})}{(V_{GAS})}\right) \times \frac{760}{Pamb}.$$

2. The method of claim 1 and further including a step of calibrating the oxygen sensor by:

(a) at the time of factory setup:
  (i) storing a psychometric table in the memory of the microprocessor based controller whereby percentage water vapor in ambient air can be derived from measured values of relative humidity, barometric pressure and temperature;

(b) in the field:
  (i) measuring relative humidity, temperature, barometric pressure and the $CO_2$ concentration at the site of the field calibration;
  (ii) performing a table look-up operation to obtain percent water vapor in ambient air sample;

(iii) computing correction factor to be applied to percentage of $O_2$ in dry air to arrive at percentage of $O_2$ in ambient air due to water vapor and level of $CO_2$ and $N_2$ in sample of ambient air; and (iv) using computed correction factor as a span adjustment factor and zero as an offset value.

* * * * *